(12) United States Patent
Zhao

(10) Patent No.: US 11,517,293 B2
(45) Date of Patent: *Dec. 6, 2022

(54) NEGATIVE-PRESSURE PARACENTESIS SYRINGE AND USE THEREOF

(71) Applicant: Hangzhou Sightnovo Medical Technology Co,. Ltd., Hangzhou (CN)

(72) Inventor: Chan Zhao, Beijing (CN)

(73) Assignee: Hangzhou Sightnovo Medical Technology Co., Ltd., Hangzhou (CN)

( * ) Notice: Subject to any disclaimer, the term of this patent is extended or adjusted under 35 U.S.C. 154(b) by 263 days.

This patent is subject to a terminal disclaimer.

(21) Appl. No.: 16/852,783

(22) Filed: Apr. 20, 2020

(65) Prior Publication Data

US 2020/0261065 A1 Aug. 20, 2020

Related U.S. Application Data

(63) Continuation of application No. 14/915,215, filed as application No. PCT/CN2015/089204 on Sep. 8, 2015, now Pat. No. 10,660,618.

(30) Foreign Application Priority Data

Sep. 9, 2014 (CN) .......................... 201420512835.0

(51) Int. Cl.
*A61B 10/00* (2006.01)
*A61F 9/007* (2006.01)

(52) U.S. Cl.
CPC .......... *A61B 10/0045* (2013.01); *A61F 9/007* (2013.01); *A61F 9/00736* (2013.01); *A61M 2210/0612* (2013.01)

(58) Field of Classification Search
CPC ........ A61B 5/150732; A61B 5/150572; A61B 5/150496; A61B 5/150488;
(Continued)

(56) References Cited

U.S. PATENT DOCUMENTS 3,503,386 A * 3/1970 Pieratt .................... A61B 5/154
600/577
4,079,729 A * 3/1978 Cornell ............ A61B 5/150496
600/584

(Continued)

FOREIGN PATENT DOCUMENTS

CN 2155813 Y * 3/1993 ............... A61B 5/14
CN 2863042 Y 1/2007
(Continued)

OTHER PUBLICATIONS

International Preliminary Report on Patentability, dated Mar. 14, 2017, for PCT Application No. PCT/CN2015/089204, filed Sep. 8, 2015, 6 pages.

(Continued)

*Primary Examiner* — Daniel L Cerioni
*Assistant Examiner* — Raymond P Dulman
(74) *Attorney, Agent, or Firm* — Morrison & Foerster LLP

(57) ABSTRACT

The present invention discloses a disposable negative-pressure anterior chamber Paracentesis syringe which belongs to the technical field of medical supplies. It comprises nine parts, including a needle cap, a Paracentesis syringe, a needle base, an internal needle, a protective cover of the internal needle, an airlock, a needle tube, a collection tube and a collection tube rack. The invention has the advantages that it fixes the Paracentesis syringe during puncture and limits the depth of the needle insertion, releases the aqueous humor slowly to prevent a sudden drop of the intraocular pressure, reduces the risk of the intraocular infection by separating the anterior chamber from outside and the collection tube can collect and store the aqueous humor directly.

15 Claims, 2 Drawing Sheets

(58) Field of Classification Search
CPC .......... A61B 5/150389; A61B 5/15003; A61B 5/154; A61B 10/0045; A61F 9/00736; A61F 9/00745; A61F 9/00754; A61F 9/00763; A61F 2009/00842–00897
See application file for complete search history.

(56) References Cited

U.S. PATENT DOCUMENTS

| | | | |
|---|---|---|---|
| 4,976,925 A * | 12/1990 | Porcher | A61B 5/150732 422/549 |
| 5,179,960 A | 1/1993 | Sarrine | |
| 6,024,710 A * | 2/2000 | Miller | G01N 33/86 604/110 |
| 6,221,078 B1 | 4/2001 | Bylsma | |
| 6,561,974 B1 | 5/2003 | Grieshaber et al. | |
| 7,772,006 B2 | 8/2010 | Tornambe et al. | |
| 10,660,618 B2 | 5/2020 | Zhao | |
| 2003/0004437 A1* | 1/2003 | Collins | A61B 5/150641 600/577 |
| 2004/0254531 A1 | 12/2004 | Carr et al. | |
| 2008/0319346 A1 | 12/2008 | Crawford et al. | |
| 2010/0241029 A1 | 9/2010 | Mahurkar | |
| 2010/0323437 A1* | 12/2010 | Nakae | A61B 5/150351 435/307.1 |
| 2012/0323142 A1 | 12/2012 | Allen et al. | |
| 2013/0317391 A1 | 11/2013 | Bullington et al. | |
| 2014/0128771 A1 | 5/2014 | Laconte et al. | |
| 2014/0171830 A1 | 6/2014 | Shaw et al. | |
| 2014/0236023 A1 | 8/2014 | Day et al. | |
| 2015/0190125 A1 | 7/2015 | Hwang | |
| 2016/0287219 A1 | 10/2016 | Zhao | |

FOREIGN PATENT DOCUMENTS

| | | | |
|---|---|---|---|
| CN | 201727638 U | 2/2011 | |
| CN | 204050005 U | 12/2014 | |
| EP | 199356 A * | 10/1986 | .......... A61B 5/1438 |
| GB | 2408456 A | 6/2005 | |
| WO | 199528881 A1 | 11/1995 | |
| WO | 2008156752 A2 | 12/2008 | |
| WO | 2013147978 A2 | 10/2013 | |

OTHER PUBLICATIONS

International Search Report and Written Opinion, dated Nov. 20, 2015, for PCT Application No. PCT/CN2015/089204, filed Sep. 8, 2015, x pages. English Translation.

Merriam-Webster Dictionary retrieved from the Internet: https://www.merriam-webster.com/dictionary/tube, last visited Feb. 27, 2018, 13 pages.

The Free Dictionary, retrieved from the Internet: https://www.thefreedictionary.com/cambered, last visited Feb. 26, 2018, 3 pages.

* cited by examiner

NEGATIVE-PRESSURE PARACENTESIS SYRINGE AND USE THEREOF

CROSS REFERENCE TO RELATED APPLICATIONS

This application is a continuation patent application of U.S. application Ser. No. 14/915,215, filed Feb. 26, 2016, which is a 371 U.S. National Phase Patent Application of PCT International Application No. PCT/CN2015/089204, filed Sep. 8, 2015, which claims priority to and the benefit of Chinese Application No. 201420512835.0, filed Sep. 9, 2014, all of which are incorporated herein by reference in their entireties.

TECHNICAL FIELD

The present invention belongs to a technical field of medical supplies, it relates to a disposable negative-pressure anterior chamber Paracentesis syringe, which is used to puncture the anterior chamber to lower the intraocular pressure and collect the aqueous humor quantitatively by the negative-pressure collection tube.

BACKGROUND

The anterior chamber paracentesis is in a technical field where the aqueous humor flows from eyes into the anterior chamber by puncturing the cornea, it has an important utilization value in the ophthalmic clinical scientific research work and is mainly used in the following three aspects: (1) lowering the intraocular pressure; (2) collecting the aqueous humor; (3) other therapeutic anterior chamber drainage.

Firstly, the anterior chamber paracentesis can lower the intraocular pressure, it can be applied to the following circumstances: a treatment for transient lowering of the intraocular pressure of the angle-closure glaucoma, the open-angle glaucoma, the secondary glaucoma and some other diseases of the ocular hypertension; a adjuvant therapy of the glaucoma trabeculectomy; the acute central retinal artery occlusion and so on. Theoretically, it will cause acute anterior optic nerve ischemia or central retinal vein occlusion when the intraocular pressure is greater than 40 mmHg, if the intraocular pressure is greater than 70 mmHg for several minutes, it will cause central retinal artery atrophy and occlusion, if the intraocular pressure cannot be controlled in time, it will cause dramatic decline in visual function and vision loss even worse. Therefore, when the intraocular pressure is particularly high or sudden rising, the anterior chamber paracentesis can lower the intraocular pressure effectively in a short time to protect visual function and create an Opportunity for the further treatment. The anterior chamber paracentesis can also be used to reduce severe complications resulted from the sudden lower of the intraocular pressure during the glaucoma. trabeculectomy. As to acute central retinal artery occlusion, the anterior chamber paracentesis can improve the perfusion of the retina and make the arterial embolus rush to the distal by the blood flow sometimes.

Secondly, it has important implications for the diagnosis of some eye diseases to test the aqueous humor collected by the anterior chamber paracentesis. For instance, it has an important guiding significance in collecting the aqueous humor to test pathogenic culture, cytology, pathogenic DNA etc so as to identify the infectious and non-infectious uveitis and masquerade syndrome. Furthermore, it can also be utilized in various forms of scientific research by collecting the aqueous humor.

Finally, the anterior chamber paracentesis can also be applied to the treatment of the anterior chamber drainage under the circumstance of the chemical alkali burn in eyes, the hyphema and so on.

However, there are no unified special equipments and supplies for the implementation of the anterior chamber paracentesis at present, people use a 1 ml syringe as the anterior chamber Paracentesis syringe and use a 1 ml syringe to collect the aqueous humor in the clinical practice, it has several problems as: (1) because there is no fixed support during the puncture, the 1 ml needle lacks stability in the anterior chamber and the operator needs to control the depth of the needle insertion on his own, it is easy for the novice to damage the cornea, iris, crystalline lens or any other adjacent tissues: (2) the outflow of the aqueous humor cannot be precisely controlled. If a 1 ml syringe punctures the anterior chamber in a high intraocular pressure, the aqueous humor outflows very fast due to the large pressure difference between the inside and outside of eyeballs, it causes a sudden drop of the intraocular pressure, rapid shall owing and even loss of the anterior chamber, it may lead to the iris and crystalline lens contacted with the corneal endothelium which causes the damage of the conical endothelial cells and crystalline lens. The sudden drop of the intraocular pressure also causes some severe complications such as the cyclodialysis, the edema of the ciliary body, the choroidal detachment, explosive suprachoroid cavity hemorrhage and so on: (3) the direct communication between the puncture point and outside increases the intraocular infection; (4) the aqueous humor needs to be transferred to a Eppendorf tube after collection: on one hand, there is some aqueous humor leaving in the needle tube which causes the waste of the sample, the rest of the microsamples may not be enough to accomplish subsequent inspections and research; on the other hand, it increases the risk of the sample pollution in the process of the aqueous humor transferring which may interfere the results of clinical test and research. it may reduce the rate of the endophthalmitis and sample pollution to operate the anterior chamber paracentesis and collect the aqueous humor in an operation room, but it increases a lot of additional process and inconvenience. In regard of the problems above, the anterior chamber paracentesis and the aqueous humor inspection have been greatly limited in the clinical practice at present.

In 2005, Yang Shaovuan etc. designed an anterior chamber Paracentesis syringe (patent No.: 200520125935), the Paracentesis syringe had made an improvement in the needle, it added flanks on both side of the needle to avoid deep puncture, it solved problem (1): in 2010, Li Sizhen etc., designed an anterior chamber Paracentesis syringe (patent No.: 2010201582223), it divided the Paracentesis syringe into two identical volume chambers and left a hole on the side which allowed the aqueous humor to outflow slowly, it mainly solved problem (2). To solve the four problems mentioned above comprehensively, the inventor designed a new anterior chamber Paracentesis syringe and expected to provide a safer, more convenient and functional anterior chamber paracentesis tool for the ophthalmic clinical and scientific research.

SUMMARY OF THE INVENTION

In view of the shortcomings of the prior arts, the inventor provides a new anterior chamber Paracentesis syringe after further research and plenty of experiments, the anterior chamber Paracentesis syringe solves the above-mentioned four problems in anterior chamber puncture decompression and the aqueous humor collection as follows: (1) the anterior chamber Paracentesis syringe lacks stability during operation; (2) the outflow of aqueous humor cannot be precisely controlled, it causes a sudden drop of the intraocular pressure, rapid shallowing and even loss of the anterior chamber in a high intraocular pressure; (3) the direct communication between the puncture point and outside increases the rate of the intraocular infection; (4) the aqueous humor needs to be transferred to a Eppendorf tube after collection, it leads to the waste of the sample and increases the risk of the sample pollution.

To fulfill the above-mentioned purposes, the invention proposes a solution as follows:

A disposable negative-pressure anterior chamber Paracentesis syringe, it comprises a needle cap. a Paracentesis syringe, a needle base, an internal needle, a protective cover of the internal needle, an airlock, a needle tube, a collection tube and a collection tube rack, characterized in that:

The Paracentesis syringe and the internal needle are connected integrally;

The needle base is made of hard materials and connected with the needle tube closely, the Paracentesis syringe and the internal needle penetrate and are fixed on the middle of the needle base;

The needle base is provided on the front end with a cambered surface which has a curve equal to that of a conical limbus, and is provided on the back end with a cylinder which is used to fix the protective cover of the internal needle;

The protective cover of the internal needle is made up of a soft elastic material, and is a tubular component with a closed back end and a front-end opening, the inner diameter of which is less than the cylindrical diameter of the back end of needle base;

The protective cover of the internal needle has a front section which fits over the back end of the needle base so as to reach an elastic fixation, and has a back section which fits over the internal needle completely;

The airlock is made up of a soft material which can be penetrated by the internal needle easily, the airlock has a petal shaped front end to be elastically fixed with the needle tube and not to form an airtight cavity in the front end of the airlock and the back end of the needle base;

The airlock has a back section which is expandable to seal the opening of the collection tube so that an airtight cavity is formed inside the collection tube;

The collection tube is spirally connected with the front end of the collection tube rack.

Preferably, the texture and inner and outer diameter of Paracentesis syringe and the internal needle are the same with that of a 1 ml syringe.

Preferably, the size of the collection tube is the same with that of a 0.5 ml Eppendorf tube.

Preferably, the protective cover of the internal needle is made by rubber.

Preferably, the Paracentesis syringe is an integrated and fully sealed design. in a preferred embodiment, the aqueous humor collection tube can be controlled by negative pressure, In a preferred embodiment, the collection tube can be separated from the Paracentesis syringe, Preferably, the needle base has a front end which has a curve equal to that of a corneal limbus.

Preferably, the anterior chamber is separated from outside during puncture.

Preferably, the needle base has a front end whose cambered surface is fit to that of a corneal limbus.

The invention of the disposable negative-pressure anterior chamber Paracentesis syringe well solves the problems caused by the traditional 1 ml syringe in anterior chamber puncture as follows: (1) the needle base has a front end with cambered surface which has a curve equal to that of the eyeballs which can fix the Paracentesis syringe and control the depth of the needle insertion to reduce the damage of the cornea, iris and crystalline lens; (2) the aqueous humor collection tube is controlled by the negative pressure, the intraocular pressure will decline gradually as the aqueous humor outflows into the collection tube which cause the pressure of collection tube rises gradually, the aqueous humor will stop flowing out when the differential pressure achieves a balance and it releases the aqueous humor slowly and quantitatively. in addition, it can collect different volume of the aqueous humor by designing different value of the negative pressure (generally 100-300 ul) to meet the needs of different intraocular pressure level and patients with different anterior chamber depth; (3) the Paracentesis syringe is a integrated and fully sealed design, the separation of anterior chamber and outside will reduce the rate of the intraocular infection; (4) the collection tube separates from the main body after the aqueous humor collection, the aqueous humor can be used in clinical examinations or research directly which avoids waste of sample due to the aqueous humor transferring and reduces the risk of the sample pollution.

In a preferred embodiment, the rubber used to produce the protective cover of the internal needle is ABS rubber.

In a more preferred embodiment, the ABS rubber is mixed/blended with a carbon-white, that is ABS rubber mixed/blended with carbon-white, the mixing weight of a carbon-white is 0.2-10% of ABS rubber, preferably, 0.2-10% of ABS rubber.

The carbon-white is particularly preferably a modified carbon-white, the modification process is shown as follows:

(1) refluxing the carbon-white (commercially available) and the 3-glycidyl trimethoxysilane by the methylbenzene for 30 minutes to 3 hours, wherein adding the 3-glycidyl trimethoxysilane and carbon-white whose weight proportion is 0.1:1-0.1:3, then filtering and vacuum drying it at room temperature.

(2) adding the product obtained by step (1) into the DMF solvent, then adding the proportion of the 3-glycidyl trimethoxysilane Moore and the compound shown in the formula (I) as follows in 1:1 1-1:1.2, refluxing 1 to 3 hours, rinsing thoroughly with the ethyl alcohol after filtering, then vacuum drying it at room temperature and the modified silicon dioxide is obtained;

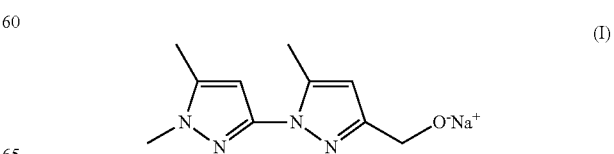

(I)

The modification process is shown in the following line:

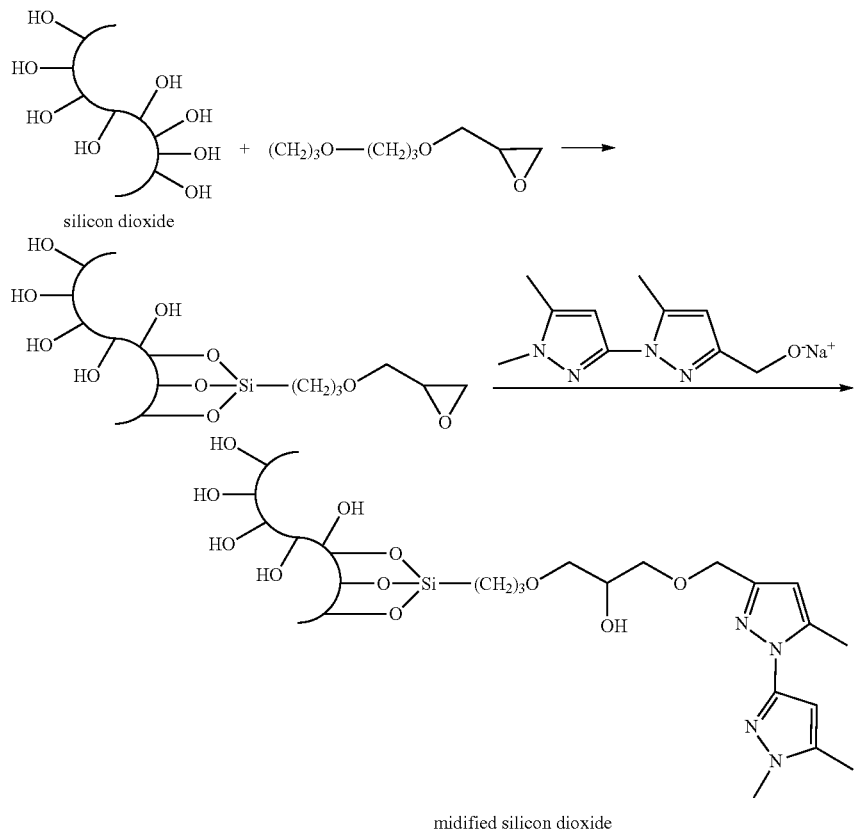

silicon dioxide midified silicon dioxide

Wherein the compound shown in formula (I) can be obtained commercially (such as purchasing from the Fluka Reagent Company), or obtaining by a conventional synthetic method of the field, such as using the 3-Amino-5-methylpyrazole by first diazotization and then reduction by the LiAlH$_4$.

The ABS rubber mixed with the carbon-white has a good performance of skid resistance which can fit over the internal needle very well; in addition, it has the most moderate elasticity, that is, has the most suitable elastic modulus which can fit over the back end of the needle base tightly, it can reach a steady elastic fixation, at the same time, avoid the installation difficulty in the productive process due to the elastic difference.

In summary, the technical solutions of the invention are non-obvious to the technicians of the field and has unexpected technical effects which include fixing the Paracentesis syringe and controlling the depth of the needle insertion during puncture, releasing the aqueous humor slowly to prevent, the sudden drop of the intraocular pressure, separating the anterior chamber from outside during puncture to reduce the risk of the intraocular infection as well as collecting and storing the anterior chamber by the collection tube directly.

BRIEF DESCRIPTION OF THE DRAWINGS

The following is a further description to the present invention in combination with the figures and embodiments.

DETAILED DESCRIPTION

Figure 1:
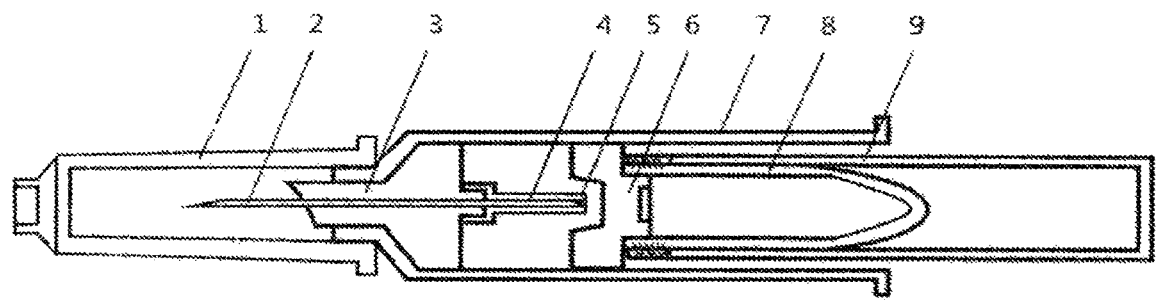
FIG. 1 is a schematic view of the structure of the disposable negative-pressure anterior chamber Paracentesis syringe.
Figure 2:
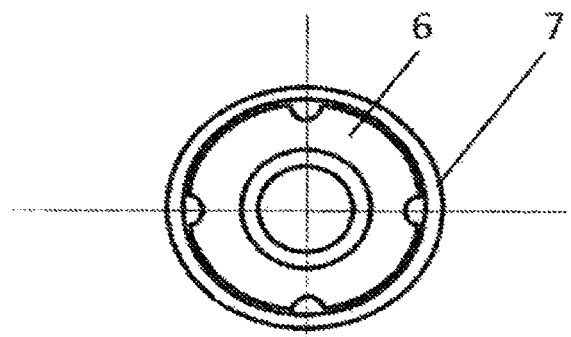
FIG. 2 is a schematic view of the relationship between the airlock left view and the needle tube.

As shown in FIG. 1, a disposable negative-pressure anterior chamber Paracentesis syringe comprises nine parts: a needle cap (1), a Paracentesis syringe (2), a needle base (3), an internal needle (4), a protective cover of the internal needle (5), an airlock (6), a needle tube (7), a collection tube and (8), a collection tube rack (9). The Paracentesis syringe (2) and the internal needle (4) are connected integrally whose texture and inner and outer diameter are the same with that of a 1 ml syringe. The needle base (3) is made of a hard material and connected with the needle tube (7) closely, the Paracentesis syringe (2) and the internal needle (4) penetrate and are fixed on the middle of the needle base (3); the front end is a cambered surface which has a curve equal to that of a corneal limbus, the cambered surface can be fixed on the corneal limbos during operation to increase the stability of the Paracentesis syringe (2) in the anterior chamber; the back end is a cylinder which is used to fix the protective cover of the internal needle (5). The protective cover of the internal needle (5) is made up of a soft elastic material, and is a tubular component with a closed back end and a front end opening, the inner diameter of which is less than the cylindrical diameter of the back end of needle base (4); The airlock (6) is made up of a soft material which can be penetrated by the internal needle easily, the airlock (6) has a petal-shaped front section to be loosely and elastically fixed with the needle tube (7) and not to form an airtight cavity in the front end of the airlock (6) and the back end of the needle base (3), the back section of the airlock is expandable to seal the opening of the collection tube (8) so that an airtight cavity is formed inside the collection tube (8); the size of the collection tube (8) is the same with that of a 0.5 ml Eppendorf tube, therefore, the commercially available centrifuge can be used to centrifuge directly. The collection tube (8) is spirally connected with the front end of the collection tube rack. (9) which is easy to disassemble.

Figure 3:
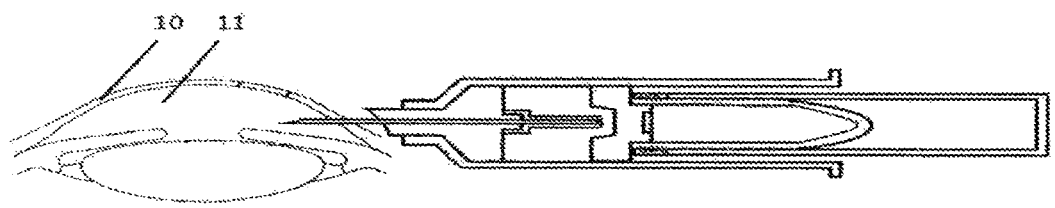
FIG. 3 is a schematic view of puncturing the anterior chamber with the disposable negative-pressure anterior chamber Paracentesis syringe.
Figure 4:
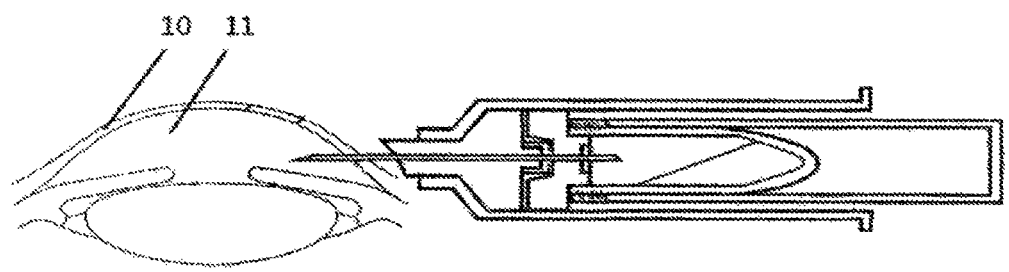
FIG. 4 is a schematic view of collecting the aqueous humor with the disposable negative-pressure anterior chamber Paracentesis syringe.

The following is the full description of the operational process of the anterior chamber puncture and the aqueous humor collection:

As shown in FIG. 3, a user holds the disposable negative-pressure anterior chamber Paracentesis syringe with the thumb and middle finger to puncture from the periphery of the cornea (10) into the anterior chamber (11), it is noted that the cambered surface of the front end of the needle base should fit to the conical limbus;

As shown in FIG. 4, the user taps the rear end of the collection tube rack (9) with the index finger, the collection tube (8) moves forward in the needle tube (7), the internal needle (4) punctures the airlock (6) and then penetrates into the collection tube (8), then the protective cover of the internal needle (5) rolls up, and the aqueous humor passes the anterior chamber (11) through the Paracentesis syringe (2) and the protective cover of the internal needle (5) into the collection tube (8) due to the pressure difference between the intraocular pressure and the negative pressure of the collection tube (8); the pressure of the collection tube (8) increases as the aqueous humor inside the collection tube increases gradually, the outflow speed of the aqueous humor declines and stops eventually.

Figure 5:
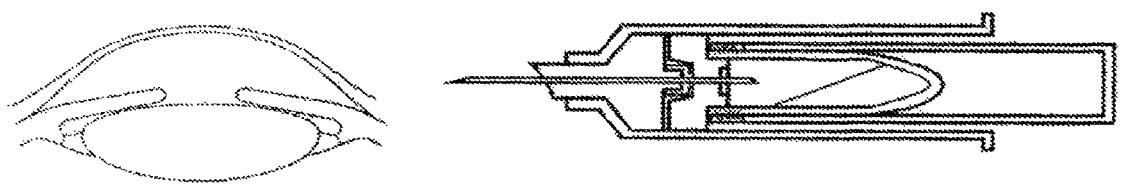
FIG. 5 is a schematic view of pulling out the disposable negative-pressure anterior chamber Paracentesis syringe.

As shown in FIG. 5, a user pulls the Paracentesis syringe (2) out from the anterior chamber (11).

Figure 6:
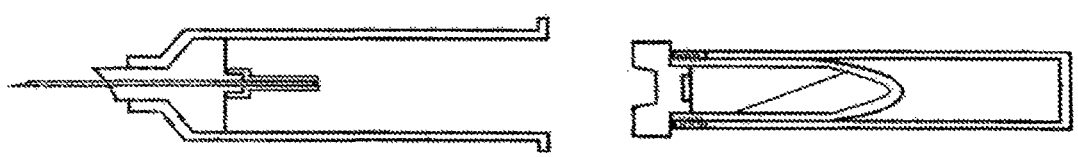
FIG. 6 is a schematic view of separating the needle tube from the collection tube.

As shown in FIG. 6, a user removes the needle tube (7) from the collection tube (8).

Figure 7:
FIG. 7 is a schematic view of separating the collection tube from the collection tube rack.

As shown in FIG. 7, a user removes the collection tube (8) from the collection tube rack (9). The aqueous humor in the collection tube (8) can be used for inspection and cryo-preservation directly.

Finally, it should be noted that: obviously, the above-mentioned embodiments are examples only for clear explanation of the present application and cannot be taken as a limitation to the embodiments. For an ordinary person skilled in the art, there are some other different forms of changes or alterations can be made based on the description mentioned above. There is no need and no way to list all the embodiments here. Those changes or alterations obviously derived from them still belong to the protection scope of the invention.

The invention claimed is:

1. A paracentesis syringe, comprising:
a needle having a paracentesis end and an internal portion;
a needle base configured to hold the needle;
a syringe barrel, within which the needle base is at least partially fitted;
a collection tube having an opening and a body for collecting aqueous humor;
an airlock situated at the opening of the collection tube, wherein the airlock is configured to engage the syringe barrel and, when in use, to be penetrated by the internal portion of the needle; and
a collection tube rack connected to the collection tube and configured to move the collection tube and the airlock along the syringe barrel.

2. The paracentesis syringe of claim 1, wherein the paracentesis end of the needle is configured to penetrate a corneal limbus.

3. The paracentesis syringe of claim 1, wherein the needle penetrates through and is fixed in the needle base.

4. The paracentesis syringe of claim 1, further comprising a protective cover configured to cover the internal portion of the needle.

5. The paracentesis syringe of claim 4, wherein the protective cover is connected to the needle base and extends to cover the internal portion of the needle.

6. The paracentesis syringe of claim 5, wherein the needle base has a front end and a back end, wherein the front end of the needle base has a cambered surface configured to fit on a corneal limbus, a curve of the cambered surface being substantially equal to a curve of the corneal limbus.

7. The paracentesis syringe of claim 6, wherein the back end of the needle base is provided with a cylinder configured to fix the protective cover thereon.

8. The paracentesis syringe of claim 1, wherein the collection tube is operated by a negative pressure.

9. The paracentesis syringe of claim 1, wherein the airlock has a front end and a back section, wherein the front end of the airlock has a first concave configured for receiving the internal portion of the needle to penetrate therethrough.

10. The paracentesis syringe of claim 9, wherein the back section of the airlock has a second concave configured for the internal portion of the needle to penetrate therethrough.

11. The paracentesis syringe of claim 1, wherein the collection tube is a 0.5 mL collection tube.

12. The paracentesis syringe of claim 4, wherein the protective cover comprises rubber.

13. The paracentesis syringe of claim 1, wherein the collection tube can be separated from the syringe barrel.

14. A method for collecting aqueous humor from a cornea, comprising:
providing the paracentesis syringe of claim 1;
puncturing into an anterior chamber of a cornea with the paracentesis end of the needle;
pushing the collection tube rack towards the needle, such that the internal portion of the needle penetrates through the airlock into the collection tube;
allowing aqueous humor from the cornea to pass through the needle and flow into the collection tube under a pressure difference between an intraocular pressure and a negative pressure of the collection tube;
pulling the paracentesis syringe out from the anterior chamber; and
removing the collection tube and the collection tube rack from the syringe barrel.

15. The method of claim 14, further comprising removing the collection tube from the collection tube rack.

\* \* \* \* \*